(12) United States Patent
Strzepa et al.

(10) Patent No.: US 8,876,901 B2
(45) Date of Patent: *Nov. 4, 2014

(54) ARTICULAR CARTILAGE IMPLANTS

(75) Inventors: Peter Strzepa, Austin, TX (US);
Stephen D. Cook, New Orleans, LA (US)

(73) Assignee: Moirai Orthopaedics, LLC, Metairie, LA (US)

( * ) Notice: Subject to any disclaimer, the term of this patent is extended or adjusted under 35 U.S.C. 154(b) by 177 days.

This patent is subject to a terminal disclaimer.

(21) Appl. No.: 13/446,984

(22) Filed: Apr. 13, 2012

(65) Prior Publication Data

US 2012/0203342 A1 Aug. 9, 2012

Related U.S. Application Data

(60) Division of application No. 12/396,872, filed on Mar. 3, 2009, now Pat. No. 8,177,842, which is a continuation-in-part of application No. 12/074,770, filed on Mar. 6, 2008, now Pat. No. 8,043,375.

(51) Int. Cl.
| | |
|---|---|
| *A61F 2/08* | (2006.01) |
| *A61F 2/28* | (2006.01) |
| *A61F 2/30* | (2006.01) |
| *A61F 2/42* | (2006.01) |
| *A61F 2/38* | (2006.01) |
| *A61F 2/40* | (2006.01) |

(52) U.S. Cl.
CPC ... *A61F 2/30756* (2013.01); *A61F 2310/00173* (2013.01); *A61F 2310/00161* (2013.01);

(Continued)

(58) Field of Classification Search
CPC .................. A61F 2/30756; A61F 2002/30112; A61F 2002/30299; A61F 2002/30822

USPC .......................... 623/14.12, 18.11, 23.44, 23.48
See application file for complete search history.

(56) References Cited

U.S. PATENT DOCUMENTS

| 4,021,864 A | 5/1977 | Waugh |
|---|---|---|
| 4,158,894 A | 6/1979 | Worrell |

(Continued)

FOREIGN PATENT DOCUMENTS

| CA | 2232068 | 3/1997 |
|---|---|---|
| DE | 69732500 | 7/2006 |

(Continued)

OTHER PUBLICATIONS

"Pyrocarbon-Information for Surgeons: Advanced Materials for Extremities Orthopedics" downloaded from http://www.pyrocarbon.com/index.php on Feb. 12, 2008; 4 pages.

(Continued)

*Primary Examiner* — David H Willse
*Assistant Examiner* — Javier Blanco
(74) *Attorney, Agent, or Firm* — Frommer Lawrence & Haug LLP; Stephen J. Lieb; Russell A. German (57) ABSTRACT

Implant devices having an articular end for repair of articular cartilage defects are provided. The articular end has an oval perimeter, a convex upper face, and a concave lower face. The convex upper face has a first circular pitch radius and a first circular roll radius. At least a portion of the concave lower face has a spherical radius, the convex upper face blending into a rim, wherein at least a first and second portion of the rim extends at least a first distance along a vertical axis and a third and fourth portion of the rim tapers inward along the vertical axis, the rim blending into the concave lower face. The articular cartilage implant devices further include a stem extending from the concave lower face away from the convex upper face along the vertical axis. The stem has a plurality of oval shaped perimeters along the vertical axis.

12 Claims, 3 Drawing Sheets

(52) U.S. Cl.
CPC .............. *A61F 2002/30112* (2013.01); *A61F 2230/0008* (2013.01); *Y10S 623/908* (2013.01); *A61F 2002/30878* (2013.01); *A61F 2310/00179* (2013.01); *A61F 2/4261* (2013.01); *A61F 2310/00574* (2013.01); *A61F 2002/30125* (2013.01); *A61F 2310/00011* (2013.01); *A61F 2002/30299* (2013.01); *A61F 2002/30822* (2013.01); *A61F 2/3804* (2013.01); *A61F 2310/00796* (2013.01); *A61F 2230/0093* (2013.01); *A61F 2/38* (2013.01); *A61F 2/40* (2013.01)
USPC ................ 623/14.12; 623/23.44; 623/908

(56) References Cited

U.S. PATENT DOCUMENTS

| | | | |
|---|---|---|---|
| 4,231,121 A | 11/1980 | Lewis | |
| 4,281,419 A | 8/1981 | Treace | |
| 4,488,843 A | 12/1984 | Achille | |
| 4,849,692 A | 7/1989 | Blood | |
| 4,919,667 A | 4/1990 | Richmond | |
| 4,945,305 A | 7/1990 | Blood | |
| 4,964,867 A | 10/1990 | Boger | |
| 5,019,104 A | 5/1991 | Whiteside et al. | |
| 5,092,896 A | 3/1992 | Meuli et al. | |
| 5,236,462 A | 8/1993 | Mikhail | |
| 5,246,460 A | 9/1993 | Goodfellow et al. | |
| 5,253,987 A | 10/1993 | Harrison | |
| 5,263,987 A | 11/1993 | Shah | |
| 5,306,311 A | 4/1994 | Stone | |
| 5,358,525 A | 10/1994 | Fox | |
| 5,383,937 A | 1/1995 | Mikhail | |
| 5,580,353 A | 12/1996 | Mendes et al. | |
| 5,600,330 A | 2/1997 | Blood | |
| 5,609,640 A | 3/1997 | Johnson | |
| 5,645,605 A | 7/1997 | Klawitter | |
| 5,683,466 A | 11/1997 | Vitale | |
| 5,742,394 A | 4/1998 | Hansen | |
| 5,744,953 A | 4/1998 | Hansen | |
| 5,749,874 A | 5/1998 | Schwartz | |
| 5,766,259 A | 6/1998 | Sammarco | |
| 5,767,669 A | 6/1998 | Hansen et al. | |
| 5,767,960 A | 6/1998 | Orman et al. | |
| 5,782,835 A | 7/1998 | Hart | |
| 5,782,927 A | 7/1998 | Klawitter et al. | |
| 5,824,095 A | 10/1998 | Di Maio et al. | |
| 5,831,260 A | 11/1998 | Hansen | |
| 5,953,683 A | 9/1999 | Hansen et al. | |
| 6,159,247 A | 12/2000 | Klawitter et al. | |
| 6,172,499 B1 | 1/2001 | Ashe | |
| 6,183,519 B1 | 2/2001 | Bonnin et al. | |
| 6,217,616 B1 | 4/2001 | Ogilvie | |
| 6,246,231 B1 | 6/2001 | Ashe | |
| 6,251,143 B1 | 6/2001 | Schwartz et al. | |
| 6,375,655 B1 | 4/2002 | Zdeblick et al. | |
| 6,417,839 B1 | 7/2002 | Odell | |
| 6,436,146 B1 | 8/2002 | Hassler et al. | |
| 6,473,167 B1 | 10/2002 | Odell | |
| 6,528,991 B2 | 3/2003 | Ashe | |
| 6,575,986 B2 | 6/2003 | Overaker | |
| 6,610,067 B2 | 8/2003 | Tallarida et al. | |
| 6,626,945 B2 | 9/2003 | Simon et al. | |
| 6,626,950 B2 | 9/2003 | Brown | |
| 6,663,669 B1 | 12/2003 | Reiley | |
| 6,679,917 B2 | 1/2004 | Ek | |
| 6,699,292 B2 | 3/2004 | Ogilvie et al. | |
| 6,709,460 B2 | 3/2004 | Merchant | |
| D490,900 S | 6/2004 | Ogilvie et al. | |
| 6,754,596 B2 | 6/2004 | Ashe | |
| 6,784,660 B2 | 8/2004 | Ashe | |
| 6,797,006 B2 | 9/2004 | Hodorek | |
| 6,814,757 B2 | 11/2004 | Kopylov et al. | |
| 6,815,651 B2 | 11/2004 | Odell | |
| 6,854,972 B1 | 2/2005 | Elian | |
| 6,856,823 B2 | 2/2005 | Ashe | |
| 7,027,634 B2 | 4/2006 | Odell | |
| 7,106,431 B2 | 9/2006 | Odell | |
| 7,161,686 B2 | 1/2007 | Duling et al. | |
| 7,204,854 B2 | 4/2007 | Guederian et al. | |
| 7,264,634 B2 | 9/2007 | Schmieding | |
| 7,314,488 B2 | 1/2008 | Reiley | |
| 7,618,451 B2 | 11/2009 | Berez et al. | |
| 8,012,217 B2 | 9/2011 | Strzepa et al. | |
| 8,043,375 B2 | 10/2011 | Strzepa et al. | |
| 8,092,530 B2 | 1/2012 | Strzepa et al. | |
| 8,152,847 B2 | 4/2012 | Strzepa et al. | |
| 2003/0135280 A1 | 7/2003 | Kopylov et al. | |
| 2003/0233149 A1 | 12/2003 | Hodorek | |
| 2004/0039447 A1 | 2/2004 | Simon et al. | |
| 2004/0230303 A1 | 11/2004 | Gomes et al. | |
| 2004/0230315 A1 | 11/2004 | Ek | |
| 2005/0033426 A1 | 2/2005 | Ogilvie et al. | |
| 2005/0084513 A1 | 4/2005 | Tang | |
| 2005/0137708 A1 | 6/2005 | Clark | |
| 2005/0137713 A1 | 6/2005 | Bertram | |
| 2006/0069446 A1 | 3/2006 | Ragusa et al. | |
| 2006/0190002 A1 | 8/2006 | Tallarida et al. | |
| 2006/0229726 A1 | 10/2006 | Ek | |
| 2006/0241778 A1 | 10/2006 | Ogilvie | |
| 2007/0005143 A1 | 1/2007 | Ek et al. | |
| 2007/0032876 A1 | 2/2007 | Clark | |
| 2007/0078334 A1 | 4/2007 | Scully et al. | |
| 2007/0123993 A1 | 5/2007 | Hassler et al. | |
| 2007/0198095 A1 | 8/2007 | VanDer Meulen et al. | |
| 2007/0225820 A1 | 9/2007 | Thomas et al. | |
| 2007/0250169 A1 | 10/2007 | Lang | |
| 2008/0188942 A1 | 8/2008 | Brown et al. | |
| 2009/0228106 A1 | 9/2009 | Strzepa et al. | |
| 2009/0240336 A1 | 9/2009 | Vander Meulen et al. | |
| 2011/0054609 A1 | 3/2011 | Cook et al. | |
| 2011/0257756 A1 | 10/2011 | Strzepa et al. | |
| 2012/0046753 A1 | 2/2012 | Cook et al. | |

FOREIGN PATENT DOCUMENTS

| | | |
|---|---|---|
| DE | 602004003510 | 8/2007 |
| DE | 60126129 | 11/2007 |
| EP | 1112753 | 2/2001 |
| EP | 1437104 | 7/2004 |
| EP | 1955676 | 8/2008 |
| EP | 2262450 | 12/2010 |
| ES | 2141533 | 3/2000 |
| JP | 2004202233 | 7/2004 |
| WO | WO 8802844 | 4/1988 |
| WO | WO 9012276 | 10/1990 |
| WO | WO 9203117 | 3/1992 |
| WO | WO 9409280 | 4/1994 |
| WO | WO 9602008 | 1/1996 |
| WO | WO 9710780 | 3/1997 |
| WO | WO 9819637 | 5/1998 |
| WO | WO 0013617 | 3/2000 |
| WO | WO 0133162 | 5/2001 |
| WO | WO 0170138 | 9/2001 |
| WO | WO 2004093767 | 11/2001 |
| WO | WO 0243627 | 6/2002 |
| WO | WO 2007041678 | 4/2007 |
| WO | WO 2007059459 | 5/2007 |
| WO | WO 2007103362 | 9/2007 |
| WO | WO 2007109752 | 9/2007 |
| WO | WO 2009111624 | 9/2009 |
| WO | WO 2010003015 | 1/2010 |
| WO | WO 2011025828 | 3/2011 |

OTHER PUBLICATIONS

"Pyrocarbon-Information for Surgeons: Pyrocarbon in Orthopedics", downloaded from www.pyrocarbon.com/pyrocarbon-orthopedic-implants.php on Feb. 12, 2008, 4 pages.

"Pyrolytic Carbon" downloaded from http://en.wikipedia.org/wiki/Pyrolytic_carbon on Feb. 12, 2008, 2 pages.

Patent Cooperation Treaty, PCT International Search Report Issued in Connection with International Application No. PCT/US09/36159; May 13, 2009; 2 pages; Europe.

(56) References Cited

OTHER PUBLICATIONS

Patent Cooperation Treaty, PCT Written Opinion of the International Searching Authority Issued in Connection with International Application No. PCT/US09/36159; May 13, 2009; 9 pages; Europe.
Patent Cooperation Treaty, PCT International Search Report Issued in Connection with International Application No. PCT/US09/049441; Aug. 26, 2009; 2 pages; Europe.
Patent Cooperation Treaty, PCT Written Opinion of the International Searching Authority Issued in Connection with International Application No. PCT/US09/049441; Aug. 26, 2009; 6 pages; Europe.
U.S. Patent and Trademark Office, Non-Final Office Action Issued Against U.S. Appl. No. 12/074,770; Oct. 28, 2009; 8 pages; U.S.A.
U.S. Patent and Trademark Office, Non-Final Office Action Issued Against U.S. Appl. No. 12/074,770; Dec. 28, 2009; 9 pages; U.S.A.
U.S. Patent and Trademark Office, Non-Final Office Action Issued Against U.S. Appl. No. 12/074,770; Apr. 27, 2010; 12 pages; U.S.A.
U.S. Patent and Trademark Office, Final Office Action Issued Against U.S. Appl. No. 12/074,770; Aug. 31, 2010; 12 pages; U.S.A.
European Patent Office, Office Action Issued Against European Application No. 09716338.0; Oct. 19, 2010; 2 pages; Europe.
"On-X Carbon Properties" downloaded from http://www.onxlti.com/onxlti-cm-carbon-prop.html; 2 pages; Nov. 15, 2010.
U.S. Patent and Trademark Office, Non-Final Office Action Issued Against U.S. Appl. No. 12/074,770; Nov. 24, 2010; 14 pages; U.S.A.
Patent Cooperation Treaty, PCT International Search Report Issued in Connection with International Application No. PCT/US2010/046654; Nov. 29, 2010; 5 pages; Europe.
Patent Cooperation Treaty, PCT Written Opinion of the International Searching Authority Issued in Connection with International Application No. PCT/US2010/046654; Nov. 29, 2010; 8 pages; Europe.
U.S. Patent and Trademark Office, Non-Final Office Action Issued Against U.S. Appl. No. 12/319,869; Nov. 29, 2010; 16 pages; U.S.A.
U.S. Patent and Trademark Office, Non-Final Office Action Issued Against U.S. Appl. No. 12/687,672; Apr. 5, 2011; 11 pages; U.S.A.
U.S. Patent and Trademark Office, Non-Final Office Action Issued Against U.S. Appl. No. 12/687,702; Apr. 13, 2011; 7 pages; U.S.A.
U.S. Patent and Trademark Office, Non-Final Office Action Issued Against U.S. Appl. No. 12/396,872; Apr. 13, 2011; 7 pages; U.S.A.
U.S. Patent and Trademark Office, Final Office Action Issued Against U.S. Appl. No. 12/074,770; May 11, 2011; 12 pages; U.S.A.
U.S. Patent and Trademark Office, Advisory Action Issued Against U.S. Appl. No. 12/074,770; Jun. 22, 2011; 3 pages; U.S.A.
U.S. Patent and Trademark Office, Notice of Allowance and Fee(s) Due, Issued in Connection with U.S. Appl. No. 12/319,869; Jun. 24, 2011; 13 pages; U.S.A.
U.S. Patent and Trademark Office, Non-Final Office Action Issued Against U.S. Appl. No. 12/396,872; Jul. 6, 2011; 18 pages; U.S.A.
U.S. Patent and Trademark Office, Final Office Action Issued Against U.S. Appl. No. 12/687,702; Nov. 25, 2011; 6 pages; U.S.A.
U.S. Patent and Trademark Office, Notice of Allowance and Fee(s) Due Issued in Connection with U.S. Appl. No. 12/396,872; Feb. 15, 2012; 11 pages; U.S.A.
U.S. Patent and Trademark Office, Non-Final Office Action Issued Against U.S. Appl. No. 12/868,112; Feb. 16, 2012; 5 pages; U.S.A.
U.S. Patent and Trademark Office; Non-Final Office Action, Issued Against U.S. Appl. No. 12/868,112; 7 pages; U.S.A.

ARTICULAR CARTILAGE IMPLANTS

CROSS-REFERENCE TO RELATED APPLICATIONS

This patent application is a divisional patent application of prior U.S. patent application Ser. No. 12/396,872 now U.S. Pat. No. 8,177,842, filed on Mar. 3, 2009, which is a continuation-in-part of prior U.S. patent application Ser. No. 12/074,770 now U.S. Pat. No. 8,043,375, filed Mar. 6, 2008.

FIELD OF THE INVENTION

This disclosure relates generally to devices for the repair of articular cartilage defects. More particularly, this disclosure relates to implants that serve as a replacement for diseased cartilage in joints such as human knees, hips and shoulders.

BACKGROUND OF THE INVENTION

Cartilage acts as a pad between bones to reduce friction and prevent the bones from grinding against one another. Cartilage covers the articular surface of many, if not all, joints in the body. The smoothness and thickness of the cartilage are factors that determine the load-bearing characteristics and mobility of the joints. Over time, due to injury or heredity, however, lesions such as fissures, cracks or crazes can form in the cartilage. In some cases, osteochondral, the lesion penetrates to the subchondral surface of the bone. In other cases, chondral, the lesion does not penetrate to the subchondral surface of the bone. In any event, lesions generally do not repair themselves—and if any repair is made it is insufficient to heal—leading to significant pain and disability, either acutely or over time.

One approach for regenerating new cartilage is autologous chondrocyte transplantation. However, this technique is complex and relatively costly. Other techniques, aimed at repair instead of regeneration, include debridement, lavage, microfracturing, drilling, and abrasion arthroplasty. These procedures generally involve penetrating the region of vascularization in the subchondral bone with an instrument until bleeding occurs. Formation of a fibrin clot differentiates into fibrocartilage, which then covers the defect site. Some have found, however, that the resulting repair tissue is relatively weak, disorganized, and lacks the biomechanical properties of normal hyaline cartilage that typically covers the bone ends. Additionally, this technique can generally only be used on chondral defects in the presence of normal joint congruity.

An alternative approach has been to undergo a total replacement of the joint. Such total replacements, however, are costly, high risk, and involve a long recovery time. Accordingly, there is a need for alternative treatments.

SUMMARY OF THE INVENTION

Definitions

In various illustrative embodiments, the terms "vertical axis" or "vertical" mean a direction from the top of a three-dimensional object to the bottom of the three-dimensional object.

In various illustrative embodiments, the term "yaw" means a direction of rotation around the vertical axis.

In various illustrative embodiments, the terms "horizontal axis" or "horizontal" mean a direction from right of the three-dimensional object to the left of the three-dimensional object.

In various illustrative embodiments, the term "pitch" means a direction of rotation around the horizontal axis.

In various illustrative embodiments, the terms "depth axis" or "depth" mean a direction from the front of the three-dimensional object to the back of the three-dimensional object.

In various illustrative embodiments, the term "roll" means a direction of rotation around the depth axis.

In various illustrative embodiments, the term "spherical radius" means the curvature of a surface formed by a sphere having a particular radius. Accordingly, when a surface is referred to as having a spherical radius, it is meant that the surface has a curvature equal to the curvature of the surface of a sphere having a particular radius.

In various illustrative embodiments, the term "circular yaw radius" means the maximum curvature about yaw of a surface formed by a circle having a particular radius rotated about yaw.

In various illustrative embodiments, the term "circular roll radius" means the maximum curvature about roll of a surface formed by a circle having a particular radius rotated about roll.

In various illustrative embodiments, the term "circular pitch radius" means the maximum curvature about pitch of a surface formed by a circle having a particular radius rotated about pitch.

In various illustrative embodiments, the term "oval" means two semi-circles connected by two straight line segments that do not intersect and that each are tangent to each semi-circle, alternatively the term "oval" means an oblong three-dimensional closed curve having no straight segments.

In various illustrative embodiments, the term "torus" means the surface of a toriod.

In various illustrative embodiments, the term "tubular radius" refers to the radius of the tube of a torus, as opposed to the radius from the center of the torus to the center of the tube.

In various illustrative embodiments, geometric terms such as "oval", "circle", "sphere", "cylinder", and the like are used as references and for clarity of understanding, as would be understood by one of ordinary skill in the art. Accordingly, these terms should not be limited to strict Euclidean standards.

In accordance with an aspect of an illustrating embodiment of the present disclosure, an implant is provided, which includes an articular end having an oval perimeter, a convex upper face and a concave lower face. The convex upper face of the oval articular end may have a first circular pitch radius and a first circular roll radius. The concave lower face of the oval articular end may have a spherical radius. Preferably, the convex upper face blends into a rim, wherein at least first and second portions of the rim extend at least a first distance along the vertical axis and third and fourth portions of the rim taper inward along the vertical axis, and the rim further blends into the concave lower face. The implant further may include a stem extending from the concave lower face away from the convex upper face. Preferably, the stem has an oval shaped perimeter in a plane perpendicular to the vertical axis.

Those skilled in the art will further appreciate the above-mentioned advantages and superior features of the invention together with other important aspects thereof upon reading the detailed description which follows in conjunction with the drawings, in which like parts are given like reference numerals, and the vertical, horizontal and depth orientations of a given embodiment are specified explicitly in at least one drawing of the embodiment.

BRIEF DESCRIPTION OF THE DRAWINGS

The drawing figures are not necessarily to scale and certain features of the invention may be shown exaggerated in scale or in somewhat schematic form in the interest of clarity and conciseness, wherein.

DISCLOSURE OF ALTERNATIVE EMBODIMENTS

Figure 1:
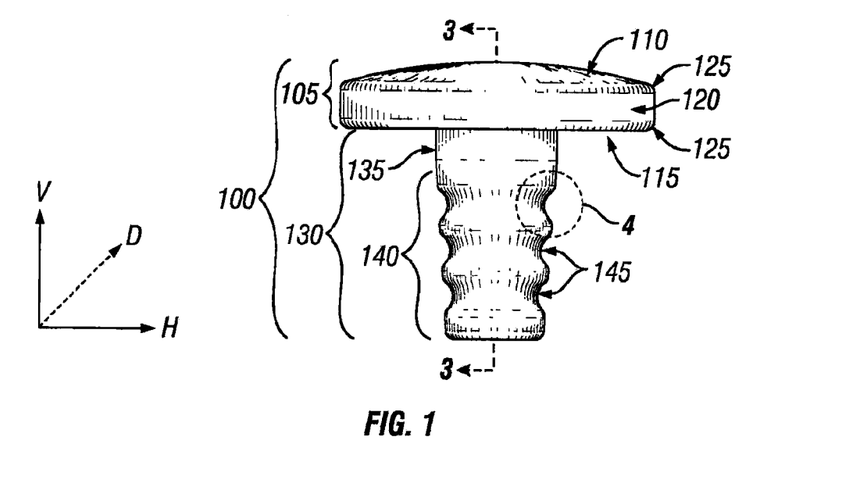
FIG. 1 is a front view of one embodiment of an implant.

FIG. 1 is an illustrative embodiment of an implant 100, in which the vertical, V, horizontal, H, and depth, D, orientations of this embodiment are depicted. The implant 100 preferably has an articular end 105 and a stem 130. The articular end 105 may be a disk of uniform thickness in the vertical or a cylinder of uniform length in the vertical. Preferably, the articular end 105 has a convex upper face 110, which blends 125 into, and is bounded by, a circular perimeter portion 120, which—after some length—itself blends 125 into a concave lower face 115.

In this embodiment, the circular pitch radius of the convex upper face 110 is about the same as the circular roll radius of the convex upper face 110. The circular pitch radius and the circular roll radius of the convex upper face 110 may be from about 25 to about 40 millimeters, alternatively from about 30 to about 35 millimeters, alternatively from about 28 to about 32 millimeters. In an embodiment, the circular pitch radius and the circular roll radius of the convex upper face 110 are approximately equal, i.e., the convex upper face 110 may have a spherical radius. The convex upper face 110 may blend, as at 125, into the circular perimeter 120, with the blend 125 having an edge radius of from about 0.1 millimeters to about 1 millimeter. Alternatively, the blend may be about 0.5 millimeters.

Figure 2:
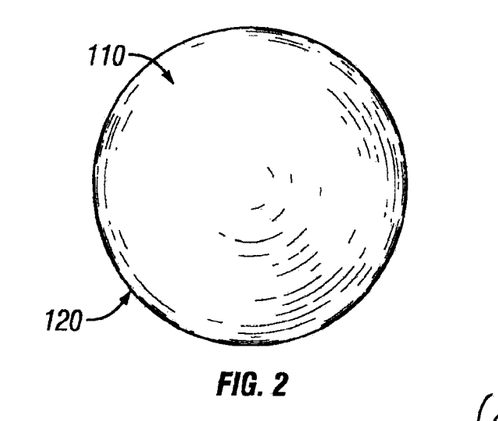
FIG. 2 is a top-down view of the embodiment of FIG. 1.
Figure 3:
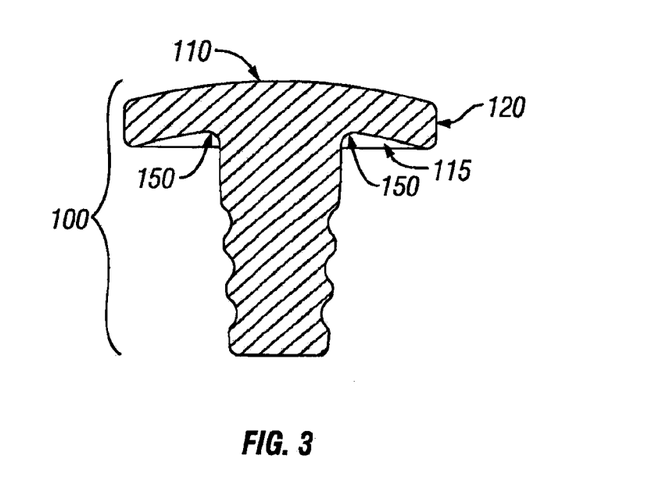
FIG. 3 is a cut-away view of the implant of FIG. 1 taken along line 3-3.

The circular perimeter 120 may extend some distance along the vertical axis, thereby forming a cylinder between the convex upper face 110 and the concave lower face 115. The length of the cylinder formed by the circular perimeter 120 may range from about one millimeter to about 5 millimeters, and alternatively from about 2 millimeters to about 3 millimeters. Referring to FIG. 2, the diameter of the circular perimeter 120 may be of any length, and may range from about 10 millimeters to about 30 millimeters, alternatively from about 12 millimeters to about 20 millimeters. Alternative diameters of the circular perimeter 120 include about 12.5 millimeters, about 15 millimeters, about 17.5 millimeters, and about 20 millimeters.

In alternative embodiments, implants 100 having circular perimeters with relatively large diameters may have convex upper faces with relatively small spherical radii. In an embodiment, relatively large diameters of circular perimeters are greater than about 17 millimeters. In an embodiment, relatively small spherical radii of convex upper faces are less than about 30 millimeters. Conversely, in alternative embodiments, implants 100 having circular perimeters with relatively small diameters may have convex upper faces with relatively large spherical radii. In an embodiment, relatively small diameters of circular perimeters are less than about 17 millimeters. In an embodiment, relatively large spherical radii of convex upper faces are greater than about 30 millimeters. In embodiments wherein the diameter of the circular perimeter 120 ranges from about 10 millimeters to about 15 millimeters, the convex upper face 110 may have a spherical radius ranging from about 30 millimeters to about 40 millimeters, preferably about 32 millimeters. In embodiments wherein the diameter of the circular perimeter 120 ranges from about 17.5 millimeters to about 20 millimeters the convex upper face 110 may have a spherical radius ranging from about 25 millimeters to about 30 millimeters, preferably about 28 millimeters. Continuing with respect to FIG. 1, in a further embodiment, the circular perimeter 120 may blend 125 into the concave lower face 115. Alternatively, the blend 125 is an edge radius of from about 0.1 millimeters to about 1 millimeter, alternatively about 0.5 millimeters.

The circular pitch radius of the concave lower face 115 may be about the same as the circular roll radius of the concave lower face 115. In this embodiment, the circular pitch radius and the circular roll radius of the concave lower face 115 may be of any length, and may range from about 20 to about 40 millimeters, alternatively from about 25 to about 35 millimeters. An alternative circular pitch radius and circular roll radius of the concave lower face 115 is about 29.5 millimeters. In embodiments wherein the diameter of the circular perimeter 120 is relatively small, the circular pitch and roll radii of the convex upper face 110 may be greater than the circular pitch and roll radii of the concave lower face 115. Further, in embodiments wherein the diameter of the circular perimeter 120 is relatively small, the convex upper face 110 may have a spherical radius of about 32 millimeters and the concave lower face may have a spherical radius of about 29.5 millimeters. In embodiments wherein the diameter of the circular perimeter 120 is relatively large, the circular pitch and roll radii of the convex upper face 110 may be lesser than the circular pitch and roll radii of the concave lower face 115. Further, in an embodiment wherein the diameter of the circular perimeter 120 is relatively large, the convex upper face 110 may have a spherical radius of about 28 millimeters and the concave lower face may have a spherical radius of about 29.5 millimeters.

In an embodiment, the circular pitch and roll radii of the convex upper face 110 are about concentric with the circular pitch and roll radii of the concave lower face 115. In an embodiment, wherein the diameter of the circular perimeter 120 is relatively small, the convex upper face 110 and the concave lower face 115 may have spherical radii of about 32 millimeters and about 29.5 millimeters, respectively. In this embodiment, spherical radii of the convex upper face 110 and the concave lower face 115 may be approximately concentric, and the centers of the spherical radii of the convex upper face 110 and the concave lower face 115 both may lie on the central vertical axis of symmetry of the implant 100, at the same point or nearly the same point. In an embodiment, wherein the diameter of the circular perimeter 120 is relatively large, the convex upper face 110 and the concave lower face 115 may have spherical radii of about 28 millimeters and about 29.5 millimeters, respectively. In this embodiment, the convex upper face 100 and the concave lower face 115 may not be concentric and may be separated by a distance along the central vertical axis of symmetry of the implant 100 and the respective centers of the spherical radii of the convex upper face 110 and the concave lower face 115 may lie on the central vertical axis of symmetry of the implant 100. The distance of separation between the convex upper face 100 and the concave lower face 115 along the central vertical axis of symmetry may range from about 2 millimeters to about 4 millimeters and may alternatively be about 2.5 millimeters.

A stem 130 may extend from the concave lower face 115 in the vertical direction away from the convex upper face 110. Alternatively, the stem 130 blends 150 into the concave lower face 115. Alternatively, the blend 150 is a fillet radius of from about 0.1 millimeters to about 1.5 millimeters, alternatively about 0.8 millimeters. The center of the stem 130 about its yaw may be concentric with the center of the circular perimeter 120 about its yaw. The stem 130 may have a maximum stem yaw radius at the intersection of the stem 130 and the concave lower face 115. The maximum stem yaw radius may be less than the circular perimeter 120 yaw radius. In this embodiment, the stem yaw radius tapers from its maximum to a lesser stem yaw radius along the vertical length of the stem 130. In this embodiment, the stem 130 may be generally conical along its entire vertical length. In a still further embodiment, the overall vertical length of the stem 130 may be at least 50% of the diameter of the circular perimeter 120.

Alternatively, the stem 130 has a cylindrical portion 135 extending from the concave lower face 115 in the vertical direction away from the concave upper face 110, and a conical portion 140 further extending from the end of the cylindrical portion 135 in the vertical direction away from the concave upper face 110. The cylindrical portion 135 may be of any length and may have a length along its vertical axis of from about one millimeter to about 5 millimeters, alternatively from about 2 millimeters to about 3 millimeters. The cylindrical portion 135 may have a circular yaw radius of any length, alternatively from about 1 millimeter to about 5 millimeters, alternatively from about 2 millimeters to about 4 millimeters. More preferred circular yaw radii of the cylindrical portion 135 include about 2.75 millimeters, about 3.125 millimeters, about 3.5 millimeters, and about 3.875 millimeters. Without wishing to be bound by the theory, the cylindrical portion 135 is preferable as it allows for ease of manufacturing, i.e., it provides a physical structure to clamp during manufacturing.

The conical portion 140 may be of any length and preferably ranges along its vertical length from about 2 millimeters to about 15 millimeters, alternatively from about 5 millimeters to about 15 millimeters, and alternatively from about 8.5 millimeters to about 11 millimeters. In this embodiment, the maximum circular yaw radius of the conical portion 140 may be located at the intersection between the conical portion 140 and the cylindrical portion 135, and is equal to the circular yaw radius of the cylindrical portion 135. The conical portion 140 may have a yaw radii that decreases from the maximum to a minimum along its vertical axis in the direction away from the upper convex face 110. The circular yaw radii of the conical portion 140 may be of any length, and may range from about one millimeter to about 5 millimeters, alternatively from about 2 millimeters to about 3 millimeters.

Figure 4:
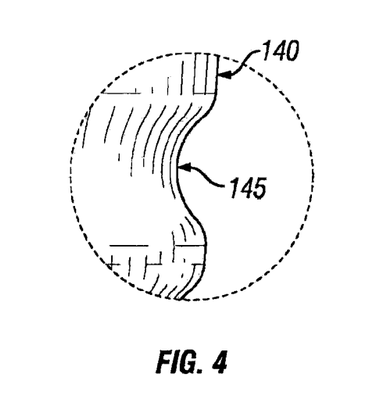
FIG. 4 is an exploded view of a portion of the front view of FIG. 1.

With respect to FIG. 4, the conical portion 140 may have circumferential grooves 145 around its perimeter. The shape of the circumferential grooves 145 may be defined by a partial torus having a tubular radius of any length, and may range from about 0.25 millimeters to about 2 millimeters, more preferably from about 0.5 millimeters to about 1 millimeter, alternatively about 1 millimeter. The circumferential grooves 145 may be spaced apart at any distance, and may be spaced apart at a distance from about 1 to about 3 millimeters from each other along the vertical, alternatively from about 2 to about 2.5 millimeters.

Figure 5:
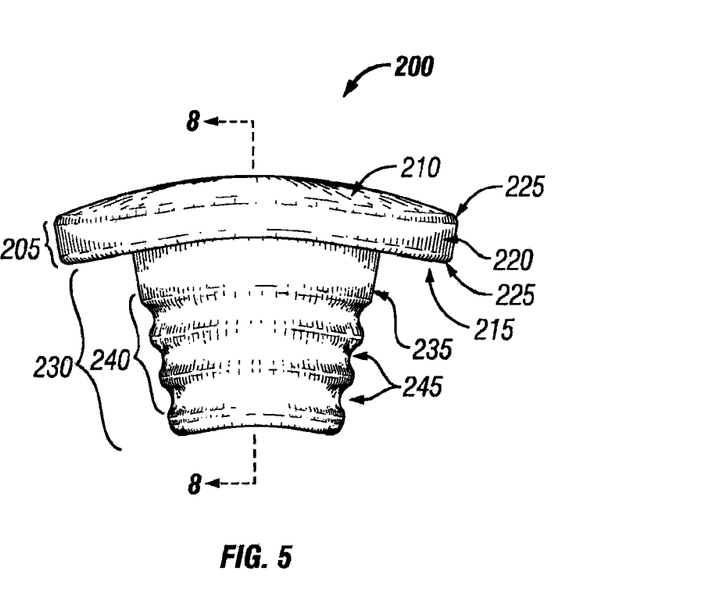
FIG. 5 is a front view of an alternative embodiment of an implant.
Figure 6:
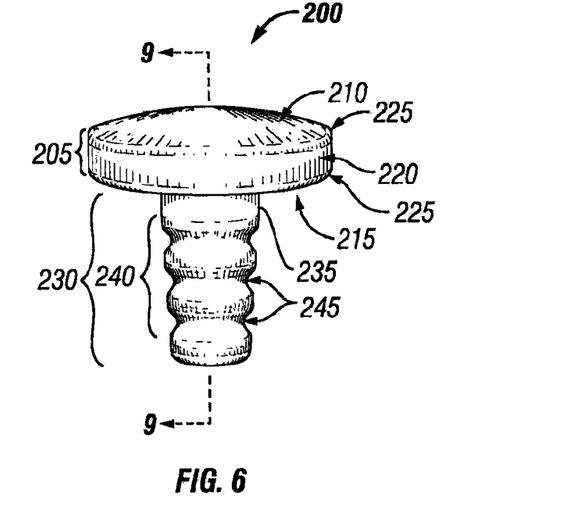
FIG. 6 is a side view of the embodiment of FIG. 5.
Figure 7:
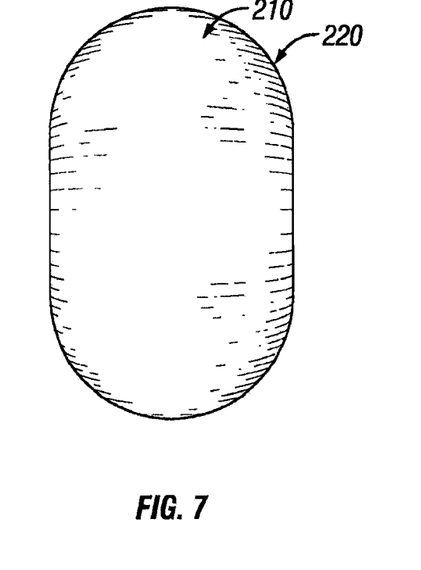
FIG. 7 is a top-down view of the embodiment of FIG. 6.

FIGS. 5 and 6 illustrate an alternative embodiment of an implant 200. The vertical, V, horizontal, H, and depth, D, orientations of this alternative embodiment of the implant 200 are depicted in FIG. 5. The implant 200 may have an articular end 205 and a stem 230. The articular end 205 may be an oval column of uniform thickness in the vertical having planar surfaces at its upper and lower faces. Alternatively, however, with respect to FIGS. 5, 6, and 7, the articular end 205 has a convex upper face 210, which blends, as at, 225 into, and is bounded by, an oval perimeter 220, which—after some length—itself blends 225 into a concave lower face 215. The blends 225 may have an edge radius from about 0.1 millimeters to about 1 millimeter. Alternatively the blends 225 may have an edge radius of about 0.5 millimeters.

With respect to FIG. 5, and in an embodiment the maximum length of the articular end 205 along the horizontal axis may be any length and may range from about 15 millimeters to about 40 millimeters, alternatively from about 20 millimeters to about 35 millimeters. Preferred maximum lengths of the articular end 205 along the horizontal axis include about 20 millimeters, about 22.5 millimeters, about 25 millimeters, about 27.5 millimeters, and about 30 millimeters. The maximum length of the articular end 205 along the depth axis may be of any length and may range from about 10 millimeters to about 30 millimeters, alternatively from about 15 millimeters to about 25 millimeters. Alternative maximum lengths of the articular end 205 along the depth axis include about 15 millimeters, about 17.5 millimeters, and about 20 millimeters. In this embodiment the maximum length of the implant 200 along the vertical axis may be of any length and may range from about 10 millimeters to about 35 millimeters, alternatively from about 10 millimeters to about 20 millimeters. In one illustrative embodiment, the maximum length of the implant 200 along the vertical axis is about 15 millimeters.

With respect to FIG. 5, the circular pitch radius of the convex upper face 210 may be of any length and may range from about 15 millimeters to about 30 millimeters, alternatively from about 20 millimeters to about 25 millimeters. An alternative length of the circular pitch radius of the convex upper face 210 is about 22 millimeters. The circular roll radius of the convex upper face 210 may be of any length and may range from about 20 millimeters to about 40 millimeters, alternatively from about 25 millimeters to about 35 millimeters. An alternative length of the circular roll radius of the convex upper face 210 is about 32 millimeters. The convex upper face 210 may have a circular pitch radius and a circular roll radius, which may be different values.

In an embodiment the curvature of the concave lower face 215 may be described as a single spherical radius. In an embodiment, the spherical radius of the concave lower face 215 ranges from about 20 to about 40 millimeters, alternatively from about 25 to about 35 millimeters, alternatively about 29.5 millimeters.

Figure 8:
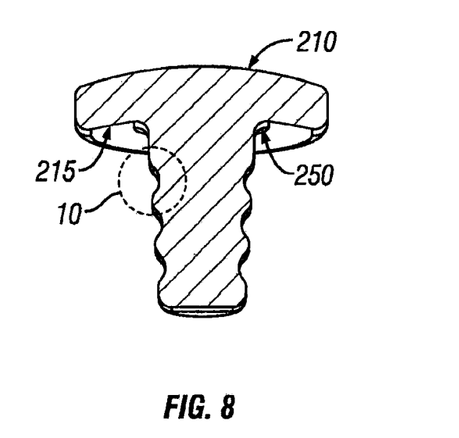
FIG. 8 is a cut-away view of the implant of FIG. 5 taken along line 8-8.
Figure 9:
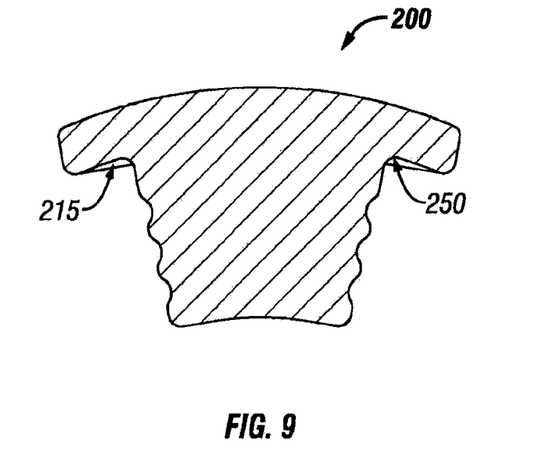
FIG. 9 is a cut-away view of the implant of FIG. 6 taken along line 9-9.

The stem 230 may have two portions, which may be both generally oval in cross-section in planes perpendicular to the vertical axis. The first portion 235 may extend from the concave lower face 215 a length along the vertical in a direction away from the convex upper face 210, and the second portion 240 extends from the end of the first portion 235 a length along the vertical in a direction away from the convex upper face 210. The stem 230 may blend 250 into the concave lower face 215 of the articular end 205. In an embodiment, the blend 250 is a fillet radius of from about 0.1 millimeters to about 1.5 millimeters, alternatively about 0.8 millimeters. The first portion 235 may be of a uniform length along the depth and of a decreasing length along the horizontal as it extends in the vertical. The first portion 235 may be of any length along the depth and may range from about 2 millimeters to about 25 millimeters, alternatively from about 5 millimeters to about 20 millimeters, alternatively from about 5 millimeters to about 10 millimeters. An alternative length along the depth of the first portion 235 is about 6.25 millimeters. The length along the horizontal of the first portion 235 may decrease from a maximum length at the intersection with the concave lower face 215 to a lesser length as it extends along the vertical. The maximum length of the first portion 235 along the horizontal may be of any length, and may range from about 5 millimeters to about 20 millimeters, alternatively from about 10 millimeters to about 15 millimeters. With respect to FIG. 8, the first portion 235 may be of any length in the vertical direction, and preferably ranges from about 2 millimeters to about 10 millimeters, alternatively from about 2 millimeters to about 8 millimeters; an alternative length of the first portion 235 in the vertical direction is about 3.6 millimeters. Without wishing to be bound by the theory, the first portion 235 is preferable as it allows for ease of manufacturing, i.e., it provides a physical structure to clamp during manufacturing.

The second portion 240 may decrease from a maximum horizontal length to lesser horizontal length as it extends in the vertical direction. The maximum horizontal length of the second portion 240 may be the same as the horizontal length of the first portion 235 at the intersection of the first 235 and second 240 portions. The second portion may decrease from a maximum length along the depth to lesser length along the depth as it extends in the vertical direction. The maximum length along the depth of the second portion 240 may be the same as the length along the depth of the first portion 235 at the intersection of the first 235 and second 240 portions, and thus may range in value as recited above with respect to the depth length of the first portion 235. With respect to FIG. 8, the second portion 240 may be of any length along the vertical direction, and may range from about 2 millimeters to about 25 millimeters, alternatively from about 5 millimeters to about 20 millimeters, alternatively from about 5 millimeters to about 10 millimeters; an alternative length of the second portion 240 along the vertical direction is about 9.1 millimeters.

Figure 10:
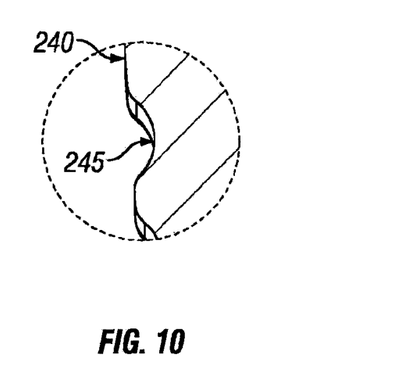
FIG. 10 is an exploded view of a portion of the cut-away view of FIG. 8.

As shown in FIG. 10, the second portion 240 may have grooves 245 about its perimeter. The shape of the grooves 245 may be defined by a partial, oval, non-planar torus having a tubular radius of any length, alternatively from about 0.25 millimeters to about 2 millimeters, alternatively from about 0.5 millimeters to about 1 millimeter. The tubular radius of the partial, oval, non-planar torus of the grooves 245 may be about 1 millimeter. Alternatively the grooves 245 are spaced apart at any distance, and may be from about 1 to about 3 millimeters from each other along the vertical, alternatively from about 2 to about 2.5 millimeters.

The implant 100 or 200 may be manufactured from a variety of suitable materials, including any of the following, individually or in combination, graphite, pyrocarbon, ceramic, aluminum oxide, silicone nitride, silicone carbide or zirconium oxide; metal and metal alloys, e.g., CO—CR—W—Ni, Co—Cr—Mo, CoCr alloys, CoCr molybdenum alloys, Cr—Ni—Mn alloys; powder metal alloys, 316L or other stainless steels, Ti and Ti alloys including Ti 6Al-4V ELI; polymers, e.g., polyurethane, polyethylene, polypropylene, thermoplastic elastomers, polyaryletherketones such as polyetherehterketone (PEEK) or polyetherketoneketone (PEKK); biomaterials such as polycaprolactone; and diffusion hardened materials such as Ti-13-13, zirconium and niobium. Moreover, the implant 100 or 200 may be coated with a variety of suitable materials, including any of the following, individually or in combination, porous coating systems on bone-contacting surfaces, hydrophilic coatings on load-bearing surfaces, hydroxyapaite coatings on bone-contacting surfaces, and tri-calcium phosphate on bone-contacting surfaces. Other suitable coatings include growth factors and other biological agents such as bone morphogenetic proteins (BMP's), transforming growth factor beta, among others. Additionally, components of the invention may be molded or cast, hand-fabricated or machined.

In one illustrative embodiment, the implant 100 or 200 is composed of graphite and pyrocarbon. The implant 100 or 200 may be graphite and may include a coating of pyrocarbon. The pyrocarbon coating may have an average thickness of from about 100 to about 1000 microns, alternatively from about 200 microns to about 500 microns, alternatively from about 250 to about 500 microns, alternatively about 350 microns. The pyrocarbon coating may have an elastic modulus from about 15 gigapascals ("GPa") to about 22 GPa, alternatively about 20 GPa. The pyrocarbon coating may further have a strength of at least 200 megapascals ("MPa"), alternatively at least about 300 MPa, alternatively at least about 400 MPa. The pyrocarbon elastic modulus and strength may be tested using a four-point bend, third-point-loading substrated specimens of dimensions 25 millimeters by 6 millimeters by 0.4 millimeters. In an embodiment, the pyrocarbon is pyrolytic carbon as described in *Pure Pyrolytic Carbon: Preparation and Properties of a New Material, On-X Carbon for Mechanical Heart Valve Prostheses*, Ely et al, J. Heart Valve Dis., Vol. 7, No. 6, A00534 (November 1998), alternatively pyrocarbon is pyrolytic carbon as described in the before-mentioned J. Heart Valve Dis. publication, but includes additional silicon.

The above-described implants may be used to repair damaged articular cartilage in humans, including knees, wrists, elbows, shoulders, and the like joints. In an illustrative method, a patient having articular cartilage damage is identified. The patient is fully informed of the risks associated of surgery, and consents to the same. An incision may be made near the damaged articular cartilage. The lesion to be repaired is identified, and an implant having dimensions compatible with the lesion is selected. The implant may be slightly smaller or slightly larger than the lesion. In these embodiments, the implant is from about 0.1 percent to about 20 percent smaller or larger than the lesion. A hole is then formed, i.e., drilled, punched, or broached, through the cartilage and the subchondral bone into the cancellous bone. Preferably, the dimensions of the hole are slightly less than the horizontal and depth dimensions of the stem of the implant. This may be achieved, for example, by using a tapered dill bit. Preferably the minimum length of the hole is equal to or slightly greater than the length of the stem of the implant, along the vertical. An amount of healthy and damaged cartilage may be removed near the lesion so that the lower portion of the implant's articular end may rest against the patient's bone. In this manner, however, it is preferable to remove as little healthy cartilage as possible. The stem of the implant may be inserted into the hole, and the lower portion of the implant's articular end may rest against the bone. The incision is then sutured by any of several known methods.

While specific alternatives to steps of the invention have been described herein, additional alternatives not specifically disclosed but known in the art are intended to fall within the scope of the invention. Thus, it is understood that other applications of the present invention will be apparent to those skilled in the art upon reading the described embodiment and after consideration of the appended claims and drawings.

The invention claimed is:

1. An articular cartilage implant comprising:

an articular end for repair of articular cartilage defects, the articular end having a perimeter, a convex upper face, and a concave lower face, the convex upper face having a first circular pitch radius and a first circular roll radius, at least a portion of the concave lower face having a spherical radius, the convex upper face blending into a rim, wherein at least a first and second portion of the rim extends at least a first distance along a vertical axis and a third and fourth portion of the rim tapers inward along the vertical axis, the rim blending into the concave lower face;

wherein the first circular pitch radius ranges from about 15 to about 30 millimeters, wherein the first circular roll radius ranges from about 20 to about 40 millimeters; and a stem extending from the concave lower face away from the convex upper face along the vertical axis, the stem having a plurality of stem perimeters along the vertical axis;

wherein the stem has a first stem portion having a maximum stem perimeter extending at least one millimeter from the concave lower face away from the convex upper face along the vertical axis, the maximum stem perimeter being less than the articular end perimeter, and a second stem portion extending from the first stem portion away from the convex upper face along the vertical axis, the second stem portion having a plurality of second stem portion perimeters decreasing in stem perimeter from the maximum stem perimeter of the first stem portion to a lesser second stem portion stem perimeter along the vertical axis of the stem; and wherein the stem has a plurality of circumferential grooves, wherein each circumferential groove extends continuously around at least one of the plurality of second stem portion perimeters, wherein at least one circumferential groove is defined between two adjacent second stem portion perimeters and has a shape of a partial, non-planar torus extending radially inward of the adjacent second stem portion perimeters, wherein the at least one circumferential groove blends into at least one of the two adjacent second stem portion perimeters, wherein the stem blends into the concave lower face, and wherein the articular end and the stem each consist essentially of: a graphite core and a pyrocarbon coating.

2. The implant of claim 1, wherein the articular end has a maximum length, along the horizontal axis of from about 15 millimeters to about 40 millimeters; the articular end has a maximum length, along the depth axis, ranging from about 10 millimeters to about 30 millimeters; and the implant has a maximum length along the vertical axis ranging from about 10 millimeters to about 35 millimeters.

3. The implant of claim 1, wherein the first portion tapers inward along its horizontal axis in the vertical direction and has a uniform length along its depth axis in the vertical direction, the second portion tapers inward along its horizontal axis and its depth axis in the vertical direction, the first and second portion blend into each other, the length of the first portion along the vertical ranges from about 2 millimeters to about 10 millimeters, the length of the second portion along the vertical ranges from about 2 millimeters to about 25 millimeters.

4. The implant of claim 1, wherein the partial, non-planar torus of the grooves has a tubular radius of from about 0.25 millimeters to about 1.5 millimeters, and the grooves are spaced apart at a distance of from about 1 millimeter to about 3 millimeters from each other.

5. The implant of claim 1, wherein the pyrocarbon coating has an elastic modulus from about 15 GPa to about 22 GPa, and the pyrocarbon coating has an average thickness ranging from about 100 to about 1000 microns.

6. The implant of claim 5, wherein the pyrocarbon coating has an elastic modulus of about 20 GPa and a strength of at least 400 MPa.

7. The implant of claim 6, wherein the upper face and perimeter of the articular end are polished, and the lower face and stem are coated with hydroxyapatite.

8. The implant of claim 1, wherein the first circular pitch radius and the first circular roll radius are about the same.

9. The implant of claim 1, wherein the perimeter of the articular end is circular.

10. The implant of claim 9, wherein the first stem portion is cylindrical and the second stem portion is conical.

11. The implant of claim 1, wherein the perimeter of the articular end is oval.

12. The implant of claim 11, wherein the maximum stem perimeter of the first stem portion is oval and the plurality of second stem portion perimeters of the second stem portion are oval.

* * * * *